United States Patent [19]

Pickering, Jr.

[11] Patent Number: 5,573,645
[45] Date of Patent: Nov. 12, 1996

[54] PROCESS AND APPARATUS FOR THE SEPARATION OF AROMATIC HYDROCARBONS

[75] Inventor: John L. Pickering, Jr., Kingwood, Tex.

[73] Assignee: Mobil Oil Corporation, Fairfax, Va.

[21] Appl. No.: 496,562

[22] Filed: Jun. 29, 1995

[51] Int. Cl.$^6$ ............................... B01D 3/00; C07C 7/04
[52] U.S. Cl. ............................... 203/25; 203/27; 203/78; 203/80; 203/DIG. 8; 203/DIG. 9; 585/805; 585/910
[58] Field of Search ................... 203/25, 2, 27, 203/78, 80, 88, DIG. 8, DIG. 9, 21; 585/805, 807, 910

[56] References Cited

U.S. PATENT DOCUMENTS

| | | |
|---|---|---|
| 2,407,820 | 9/1946 | Durrum . |
| 2,425,559 | 8/1947 | Passino et al. . |
| 2,683,761 | 7/1954 | McCaulay et al. . |
| 2,725,413 | 11/1955 | McCaulay et al. . |
| 2,922,827 | 1/1960 | Saffer et al. . |
| 3,445,537 | 5/1969 | Luther et al. . |
| 3,597,490 | 8/1971 | Otani et al. . |
| 3,639,497 | 2/1972 | Martel et al. . |
| 3,789,077 | 1/1974 | Kosseim et al. ............... 203/27 |
| 3,808,284 | 4/1974 | Wallace et al. . |
| 3,812,197 | 5/1974 | Suggitt et al. . |
| 4,041,091 | 8/1977 | Henry ............................ 203/25 |
| 4,052,476 | 10/1977 | Morrison . |
| 4,097,543 | 6/1978 | Haag et al. . |
| 4,117,026 | 9/1978 | Haag et al. . |
| 4,555,311 | 11/1985 | Ward ............................ 203/21 |
| 4,586,986 | 5/1986 | Preusser et al. ............... 203/25 |
| 4,615,769 | 10/1986 | Horigome et al. ............. 203/2 |
| 4,851,604 | 7/1989 | Absil et al. . |
| 5,173,461 | 12/1992 | Absil et al. . |
| 5,243,117 | 9/1993 | Chang et al. . |

Primary Examiner—Virginia Manoharan
Attorney, Agent, or Firm—Ronald A. Bleeker; Malcolm D. Keen

[57] ABSTRACT

A distillation process and apparatus for recovering high purity aromatic products from a mixed aromatic hydrocarbon feedstock containing benzene, toluene and xylene by use of distillation towers integrated by heat exchange whereby substantial savings in operating costs and apparatus costs are realized. The distillation apparatus includes a benzene distillation tower and heat exchanger, a first toluene distillation tower and external heater, a second toluene distillation tower and heat exchanger and a xylene distillation tower and external heater, whereby the benzene distillation tower and heat exchanger are operably connected to the first toluene distillation tower and external heater and the second toluene distillation tower and heat exchanger are operably connected to the xylene distillation tower and external heater. A feature of the integrated method and apparatus is the utilization of the overhead fraction from the first toluene distillation tower as the source of reboil heat in the benzene distillation tower, and the utilization of the overhead fraction from the xylene distillation tower as the source of reboil heat in the second toluene distillation tower. Another feature of the integrated method and apparatus of the invention is the operation of the first toluene distillation tower at an elevated temperature and pressure and the operation of the second toluene distillation at a lower temperature and pressure.

15 Claims, 2 Drawing Sheets

PRIOR PROCESS

PROCESS AND APPARATUS FOR THE SEPARATION OF AROMATIC HYDROCARBONS

FIELD OF INVENTION

The present invention is directed to a distillation process for the separation of aromatic hydrocarbons in hydrocarbon streams containing benzene, toluene and xylene. The invention is particularly directed to an improved distillation process for the separation of aromatic hydrocarbons in hydrocarbon effluent streams containing benzene, toluene and xylene obtained from petroleum refining processes and from chemical processes. The invention is more particularly directed to an improved distillation process which utilizes new and improved distillation apparatus to efficiently separate an aromatic hydrocarbon stream containing benzene, toluene and xylene into its component compound parts and in high purity.

DISCUSSION OF THE PRIOR ART

With the growing demand of high-purity aromatic products for the chemical industry, certain petroleum streams such as reformates and hydrogenated pyrolysis gasolines have become the major source of raw materials for the production of a wide variety of aromatic compounds, including but not limited to ethyl benzene, toluene, benzene and xylene. Non-aromatic hydrocarbons are also recovered from the processing of such raw materials. However, with this type of process utility costs are high as large quantities of heat are required to effect the necessary separations of the process streams. When the fractionation scheme includes a benzene-toluene-xylene distillation, the heat requirements are further increased, due to the high reflux ratios associated with this separation.

It is known that toluene has been transalkylated over various catalysts to produce a product stream containing benzene and xylene. Both the lighter benzene stream and the heavier xylene stream contain impurities most commonly including light alkyl hydrocarbons and ethyl benzene. The light alkyl hydrocarbons may typically include methyl, ethyl and propyl hydrocarbons. The ethyl benzene may include dimethyl and trimethyl benzene.

These impurities are undesirable in that they require substantial processing to remove. For example, the treatment of xylene to separate the lighter and heavier hydrocarbons may require extensive fractionation.

Further, whereas toluene is of relatively low economic value, para-xylene is a valuable commercial product useful in the production of polyester fibers. Therefore, the catalytic production of para-xylene has received a lot of attention. The synthesis of para-xylene is typically performed by transalkylation of toluene in the presence of a catalyst. The by-products of the reaction, namely benzene, unreacted toluene and ethyl benzene, however, have proven to be difficult to separate in a cost effective manner.

What has been needed is an improved energy efficient distillation process and an improved design of distillation apparatus which allows lower cost operation of the separation process.

OBJECTS OF THE INVENTION

It is an object of the present invention to provide an aromatic distillation process having substantially lower utility requirements and apparatus cost than systems and methods previously used for similar processes.

A further object is to provide a relatively inexpensive and efficient method of producing high-purity aromatic products from aromatic hydrocarbon feedstocks.

Yet another object is to provide an integrated aromatic distillation process which offers the advantage of substantial savings in capital equipment costs as well as operating costs.

It is a further object of the present invention to provide a method for the transalkylation of toluene to obtain an aromatic hydrocarbon effluent stream containing benzene, toluene and xylene and to provide an improved distillation process and distillation apparatus for the separation of the aromatic hydrocarbon stream into its component parts.

A still further object of the present invention is to provide a distillation method and apparatus which has reduced operation energy requirements and reduced equipment costs.

SUMMARY OF THE INVENTION

In accordance with the present invention, the overhead streams of the distillation towers are integrated with the heating of other distillation towers to efficiently conserve heat energy and to reduce operating cost of carrying out the distillation process. The distillation process of the invention includes in the following sequence a benzene distillation tower, a first toluene distillation tower, a second toluene distillation tower and a xylene distillation tower. Heat is provided to the first toluene distillation tower by way of an external heater. The overhead stream of the first toluene distillation tower is fed to a heat exchanger which provides reboiler heat to the benzene distillation tower to distill the benzene. Heat is provided to the xylene distillation tower by way of an external heater. The overhead stream from the xylene distillation tower is fed to a heat exchanger which provides reboiler heat to the second toluene distillation tower to distill the toluene.

The first toluene distillation tower is operated at high temperature and high pressure such that there is sufficient heat energy in the overhead toluene stream that is heat exchanged with the benzene distillation tower to carry out the benzene distillation. The second toluene distillation tower is operated at a pressure sufficiently lower than that of the first toluene distillation tower such that a portion of the toluene is flash vaporized in the second toluene distillation tower and the heat energy required to carry out the distillation of the remaining toluene in the second toluene distillation tower is significantly reduced.

In an embodiment of the invention toluene is fed to a transalkylation reactor to obtain the aromatic hydrocarbon feed to the distillation process which includes benzene, unreacted toluene and xylene. The aromatic hydrocarbon stream is separated into its component parts using the distillation process and apparatus of the present invention.

In another embodiment of the present invention an aromatic petroleum refining stream containing benzene-toluene-xylene is fed to the distillation process of the present invention to separate and recover the benzene, toluene and xylene.

ADVANTAGES OF THE INVENTION

The present invention provides an improved integrated process for the separation of an aromatic hydrocarbon stream containing benzene, toluene and xylene into its component parts which reduces operating costs and reduces apparatus cost. The present invention utilizes two relatively small toluene distillation towers of relatively low cost which can be fabricated off-site, whereas previously there had been used a single large toluene distillation tower which, because of its size, was required to be fabricated on-site at high cost.

Significant reduction in operating costs is achieved by operating the first toluene distillation tower at elevated temperature and elevated pressure and using the heated overhead toluene stream to heat exchange with the benzene distillation tower bottom fraction to distill the benzene from the benzene tower.

Further reduction in operating costs is achieved by reducing the operating pressure in the second toluene distillation tower, relative to the pressure in the first toluene distillation tower, which allows removal of a portion of the toluene from the second tower by flash vaporization.

Further advantages of the invention are set forth or rendered apparent by the following detailed description which is to be considered together with the accompanying FIG. 1 drawing which is a schematic diagram of an integrated distillation system of the invention for recovering benzene, toluene and xylene, as high purity products from an aromatic hydrocarbon feedstock.

Figure 1:
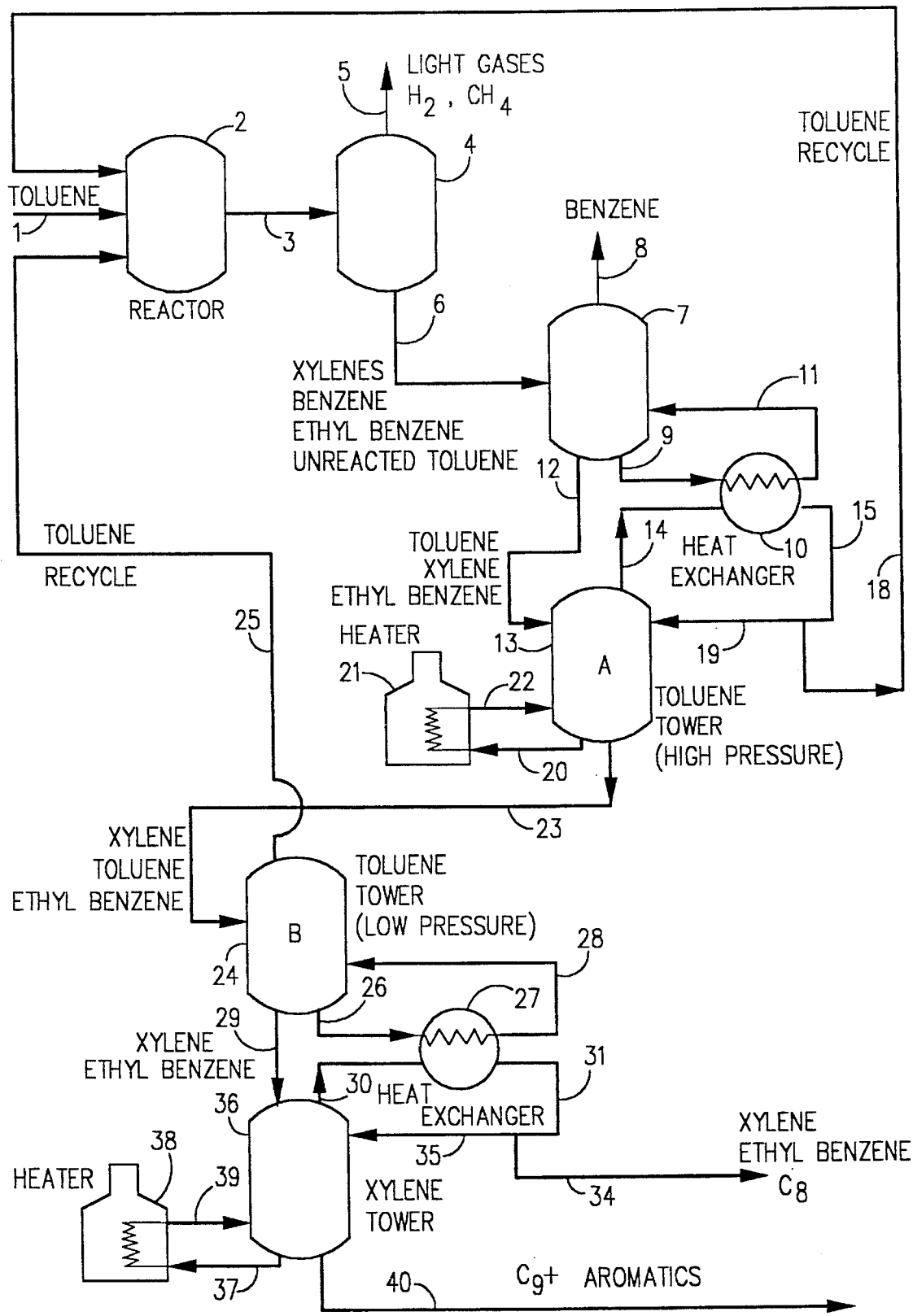
FIG. 1 of the drawings is a schematic illustration of a toluene transalkylation process and of apparatus for the separation of aromatic effluent products including a high temperature and high pressure first toluene distillation tower and a low temperature and low pressure second toluene distillation tower.

Practice of the process of this invention will be apparent to those skilled in the art from the following description of a preferred embodiment wherein, as elsewhere in this specification, all parts are parts by weight unless otherwise noted. The drawings are schematic and do not include details of auxiliary processing equipment such as pumps, heat exchangers, collection vessels, etc.

DETAILED DESCRIPTION OF THE INVENTION

An embodiment of the present invention is discussed with reference to FIG. 1 of the drawings which is a schematic illustration of a toluene transalkylation process and distillation separation process in which two toluene distillation towers are used, and includes the separation of the aromatic effluent products from a transalkylation reactor into a benzene stream, a toluene recycle stream and a mixed xylene stream containing ortho-, meta- and para-xylene.

Fresh toluene feed is fed through line 1 together with unreacted recycle toluene fed through lines 18 and 25 to the transalkylation reator 2 in which the toluene is catalytically converted by a ZSM-5 catalyst to $C_5^-$ hydrocarbons and light gases, benzene, toluene (unreacted), xylene, ethyl benzene and $C_9^+$ aromatic hydrocarbons. The transalkylation reactor 2 effluent is withdrawn through line 3 and fed to separator tower 4. The $C_5^-$ hydrocarbons and light gases including hydrogen are removed overhead through line 5. A bottom fraction stream containing benzene, toluene, xylene, ethyl benzene and $C_9^+$ aromatic hydrocarbons is withdrawn through line 6 and fed to the benzene distillation tower 7. A substantially pure benzene stream is removed overhead through line 8 and taken to further processing or to storage.

The heat for distillation in the benzene tower is provided by heat exchanger 10. A portion of the hydrocarbon bottom fraction in tower 7 is withdrawn through line 9 and reboiled in heat exchanger 10 and returned to the bottom of tower 7 through line 11 to distill the benzene in tower 7. A second portion of the bottom fraction in tower 7 which contains toluene, xylene, ethyl benzene and $C_9^+$ aromatic hydrocarbons is withdrawn through line 12 and fed a first toluene distillation tower 13, also referred to as tower (A). The first toluene distillation tower 13 is operated at a sufficiently high temperature and pressure such that an overhead stream 14 from tower 13 is sufficiently hot to provide the reboiler heat needed to carry out the distillation of benzene in tower 7.

The first toluene distillation tower 13 is heated by external heater 21. In tower 13 the hydrocarbons are separated into an overhead toluene stream and a liquid bottom fraction. The overhead toluene stream is removed through line 14 and fed to the benzene heat exchanger 10 to provide heat to reboil the bottom fraction in the benzene tower 8 to distill the benzene. The overhead toluene stream, after giving up heat in the heat exchanger 10, is removed from heat exchanger 10 and a portion of the cooled toluene is fed through lines 15 and 19 back to tower 13 to provide reflux for the toluene distillation. The portion of the cooled toluene is fed through line 18 and recycled to the transalkylation reactor 2 or to storage.

A portion of the bottom fraction in tower 13 is withdrawn through line 20 and fed to external heater 21 to be heated and returned through line 22 to tower 13 to provide the heat to carry out the toluene distillation in tower 13.

A bottom fraction is withdrawn from tower 13 through line 23 and contains the remaining toluene xylene, ethyl benzene and $C_9^+$ aromatic hydrocarbons and is fed to the second toluene distillation tower 24, also referred to as tower (B). The pressure in tower 24 is sufficiently reduced such that at least a portion of the toluene is flash vaporized.

The distillation in the second toluene distillation tower 24 is provided in part by reducing the pressure in tower 2 relative to the pressure in the first toluene distillation tower 13 and flash vaporizing the toluene and by heat added by heat exchanger 27. A portion of the hydrocarbons bottom fraction in tower 24 is withdrawn through line 26 and reboiled in heat exchanger 27 and returned to the bottom fraction of tower 24 through line 28 to distill the remaining toluene in tower 24. A second portion of the bottom fraction in tower 24 which contains xylene, ethyl benzene and $C_9^+$ aromatic hydrocarbons is withdrawn through line 29 and fed to xylene distillation tower 36. The distilled toluene is removed from tower 24 overhead through line 25 and recycled to the transalkylation reactor 2.

The hydrocarbons in the xylene distillation tower 36 are withdrawn through line 37 and heated in external heater 38 and returned to the bottom fraction of tower 36 through line 39 to provide the heat for distillation in tower 36.

The heated xylene and ethyl benzene are removed overhead through line 30 and fed to heat exchanger 27 to provide reboiler heat for the distillation of toluene in the second toluene distillation tower 24. The xylene and ethyl benzene stream, after giving up heat in the heat exchanger 27, are withdrawn through line 31. A portion of the withdrawn and cooled stream is fed through line 35 to provide reflux at the top of the xylene distillation tower 36. The remainder of the xylene and ethyl benzene stream is withdrawn through line 34 for further processing to separate the ethyl benzene and to separate the xylene into ortho-, meta-, and para-xylene.

The bottom fraction from the xylene distillation tower 36 contains $C_9^+$ aromatic hydrocarbons and is withdrawn through line 40 for further processing or disposal.

Essential requirements of the invention are that the first toluene tower (A) is operated at high, i.e. elevated, temperature and high, i.e. elevated, pressure and that the overhead toluene product provides reboiler heat to the benzene distillation tower, and that the second toluene distillation tower (B) is operated at a lower pressure, or lower pressure and lower temperature than the first toluene distillation tower. These features are integrated and necessary in order to effect the needed heat exchange to reboil the bottom fraction in the benzene distillation tower and to carry out the toluene distillation in the second toluene distillation tower.

Figure 2:
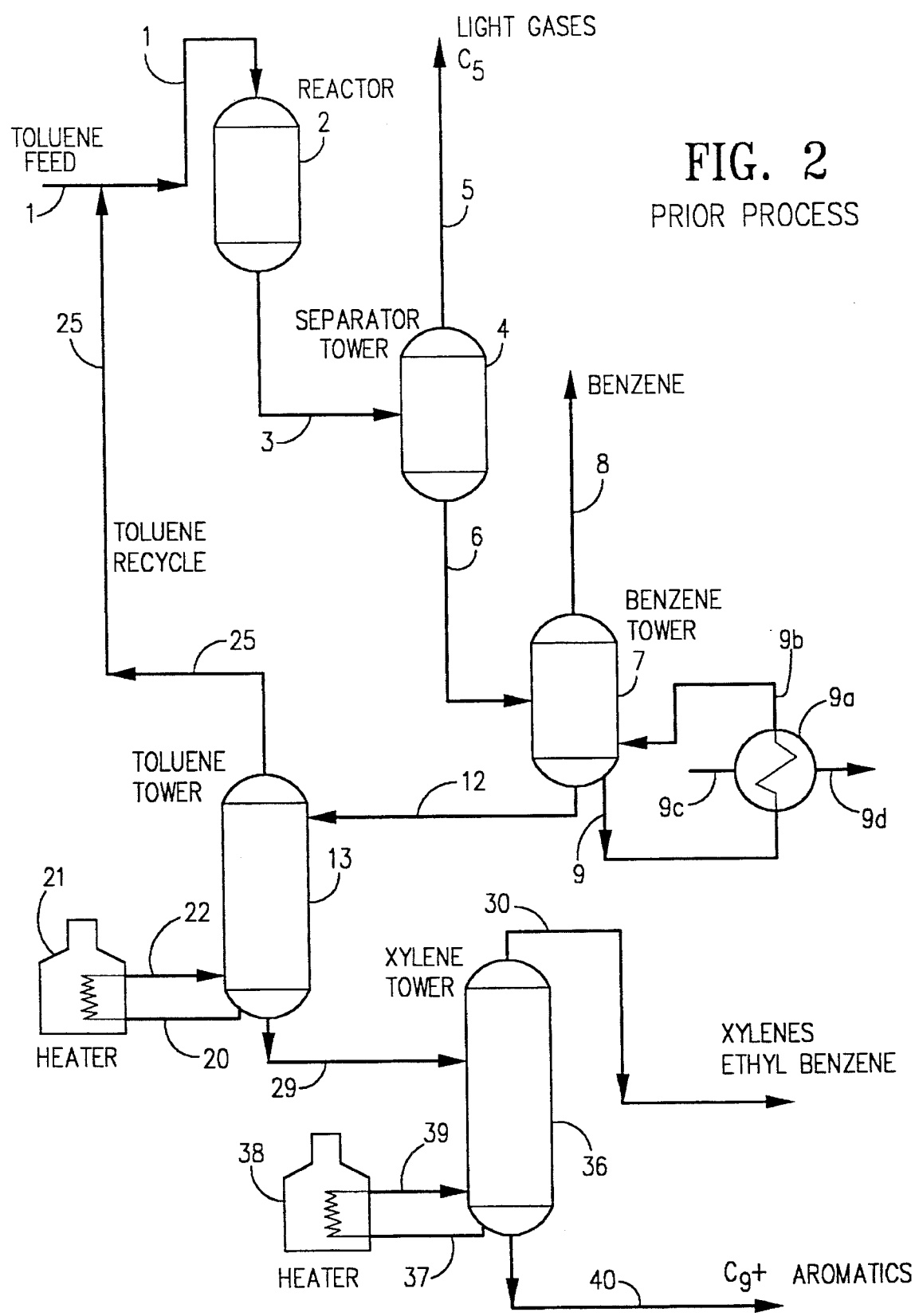
FIG. 2 of the drawings is a schematic illustration of a translakylation and distillation process previously known to applicants which includes the separation of the aromatic effluent products from a transalkylation reactor in which a large single toluene distillation tower is used.

The FIG. 2 of the drawings is a schematic illustration of a toluene transalkylation process and distillation process previously known to applicants in which a single toluene distillation tower is used and includes the separation of the aromatic hydrocarbon effluent products from the transalkylation reactor into a benzene stream, a toluene (unreacted) recycle stream and a xylene stream containing ortho-, meta- and para-xylene.

Fresh toluene feed is fed through line 1 together with unreacted recycle toluene feed fed through line 25 to the transalkylation reactor 2 in which toluene is catalytically converted by contact with a ZSM-5 catalyst to $C_5^-$ hydrocarbons and light gases, benzene, toluene (unreacted), xylene, ethyl benzene and $C_9^+$ aromatic hydrocarbons The transalkylation reactor 2 effluent is withdrawn through line 3 and fed to separation tower 4. The $C_5^-$ hydrocarbons and light gases including hydrogen are removed overhead through line 5. A bottom fraction stream containing benzene, toluene, xylene, ethyl benzene and $C_9^+$ aromatic hydrocarbons is withdrawn through line 6 and fed to the benzene distillation tower 7. A substantially pure benzene stream is removed overhead through line 8 and taken to further processing or to storage.

The heat for distillation in the benzene tower is provided by heat exchanger 9a. A portion of the hydrocarbon bottom fraction in tower 7 is withdrawn through line 9 and reboiled in heat exchanger 9a and returned to the bottom of tower 7 through line 9b. The heat is provided to heat exchanger 9b from an off-site heat source through steam line 9c and the steam is withdrawn from the heat exchanger through line 9d. A second portion of the bottom fraction in tower 7 is withdrawn through line 12 and fed to toluene distillation tower 13. In tower 13 the hydrocarbons are separated into an overhead stream containing substantially only toluene and a bottom fraction containing xylene, ethyl benzene and $C_9^+$ aromatic hydrocarbons. The distillation tower 13 distills the toluene which is taken overhead in line 25 and is recycled to the toluene transalkylation reactor 2 or is taken to storage. The heat for distillation of the toluene in toluene distillation tower 13 is provided by external heater 21. A portion of the bottom fraction of the hydrocarbons in the toluene distillation tower 13 is withdrawn through line 20 and fed to the external heater 21 and then returned through line 22 to the bottom of the distillation tower 13 to provide the heat to carry out the distillation in tower 13. A second portion of the bottom fraction of the toluene distillation tower 13 containing xylene, ethyl benzene and $C_9^+$ aromatic hydrocarbons is withdrawn though line 29 and fed to the xylene distillation tower 36.

The hydrocarbons in the xylene distillation tower 36 are withdrawn through line 37 and heated in external heater 38 and returned to the bottom of the tower 36 through line 39 to provide the heat for distillation in tower 36.

The heated xylene and ethyl benzene are removed overhead through line 30 and taken for further processing to separate the ethyl benzene and to separate the xylene into ortho-, meta- and para-xylene.

The bottom fraction from the xylene distillation tower 36 contains $C_9^+$ aromatic hydrocarbons and is withdrawn through line for further processing or disposal.

DESCRIPTION OF THE AROMATIC HYDROCARBON FEED STOCK

The aromatic hydrocarbon feed stocks to the distillation process of the present invention can be petroleum refining process streams containing benzene, toluene and xylene.

Another source of aromatic hydrocarbon feed stocks includes the effluent product from a toluene transalkylation reaction process which contains benzene, toluene and xylene.

The composition of suitable aromatic hydrocarbon feed stocks for use in the distillation process of the present invention are given in the below Table 1.

TABLE 1

| FEED | Weight Percent TYPICALLY |
|---|---|
| $C_5^-$ | 1–2 |
| Benzene | 10–20 |
| Toluene | 55–75 |
| Xylene | 10–20 |
| Ethyl Benzene | 0.1–2 |
| $C_9^+$ | 0.5–3 |

The $C_5^-$ component can contain $C_5$ alkyl and cycloalkyl hydrocarbons, $C_1$–$C_4$ alkyl hydrocarbons such as methane, ethane, propane and butane, and hydrogen.

The $C_9^+$ component can contain trimethyl benzene, diethyl benzene, naphthalenes, etc.

The xylene component typically contains ortho-, meta- and para-xylene and a minor amount of ethyl benzene.

PROCESS CONDITIONS

In accordance with the present invention and with reference to FIG. 1 of the drawings, an aromatic hydrocarbon feed stream comprising $C_5^-$, benzene, toluene, xylene, ethyl benzene and $C_9^+$ aromatic hydrocarbon components is fed to a separation tower operated at a temperature and pressure sufficient to separate an upper fraction $C_5^-$ stream which is taken overhead and removed.

A bottom fraction stream with the $C_5^-$ hydrocarbons removed and containing benzene, toluene, xylene, ethyl benzene and $C_9^+$ aromatic hydrocarbons is withdrawn from the separation tower and fed to a benzene distillation tower operated at a temperature and pressure sufficient to separate an upper substantially pure benzene fraction which is taken overhead and removed. A portion of a bottom fraction containing toluene, xylene, ethyl benzene and $C_9^+$ aromatic hydrocarbons is heated by heat exchange with the upper overhead stream from the first toluene distillation tower (A) to provide the heat for distillation of the benzene.

The remainder of the bottom fraction from the benzene distillation tower with the benzene removed is withdrawn and fed to the first toluene distillation tower (A) which is operated at a sufficiently high temperature and high pressure that an overhead fraction comprising toluene contains sufficient heat energy to be heat exchanged with the bottom fraction of the benzene distillation tower to provide the necessary heat for the distillation of the benzene. An overhead fraction containing a major portion of the toluene is removed through lines 15 and 18 and is taken for further treatment or to storage.

A bottom fraction from the first toluene distillation tower containing benzene, a minor amount of toluene, xylene, ethyl benzene and $C_9^+$ aromatic hydrocarbons contains sufficient heat energy such that when it is fed to a second toluene distillation tower (B) operated at a pressure sufficiently lower than the pressure in the first toluene distillation tower such that at at least a portion and preferably a signiificant portion of the toluene in the second toluene distillation tower is flash vaporized. The lower pressure of the second toluene distillation tower (B) allows the toluene to flash vaporize and reduces the cost of distilling the toluene in the second tower. The heat needed to complete the distillation of the toluene is provided by heat exchange of a portion of the bottom fraction in the second toluene distillation tower (B) with an overhead fraction from the xylene distillation tower 36. Toluene is removed overhead and recycled, or taken for further treatment or to storage.

The bottom fraction in tower (B) contains xylene, ethyl benzene and $C_9^+$ hydrocarbons and is withdrawn and fed to the xylene distillation tower which is operated at a temperature and a pressure sufficient to distill overhead the xylene and ethyl benzene. The overhead fraction in the xylene distillation tower 36 is heat exchanged with a portion of the bottom fraction in the second toluene distillation tower (B) to provide the necessary heat to distill the remainder of the toluene in the tower (B) which is withdrawn through line 25 and recycled to the reactor 3 or taken to storage. The overhead stream of xylene and ethyl benzene removed from the xylene distillation tower 36 is taken for further processing to remove the ethyl benzene and to separate the xylene into ortho-, meta- and para-xylene. A portion of the bottom fraction from xylene distillation tower 36 is cycled to an external heater 38 to be heated to provide the heat needed to carry out the distillation of the xylene and ethyl benzene from tower 36. A bottom fraction containing $C_9^+$ aromatic hydrocarbons is withdrawn from tower 36 and taken for further treatment or disposal.

With reference to FIG. 1 of the drawings, the heat provided by the benzene distillation tower heat exchanger 10 to the benzene distillation tower is sufficient to distill substantially all of benzene in the feed stream fed to the benzene distillation tower.

The heat provided to the first toluene distillation tower is sufficient to distill overhead a major portion but not all of the toluene in the bottom stream from the benzene tower feed to the first toluene distillation tower, and to provide sufficient heat in the overhead stream to distill the benzene in the benzene distillation tower.

The heat provided to the second toluene distillation tower is sufficient to distill overhead the remainder of the toluene in the bottom stream from the first distillation tower.

The heat provided to the xylene distillation tower by the xylene distillation tower heater 38 is sufficient to distill overhead the xylene and the ethyl benzene in the bottom stream from the second toluene distillation tower that is fed to the xylene distillation tower, and to provide sufficient heat energy in the overhead fraction to distill the remainder of the toluene in the second toluene distillation tower.

By comparison with the FIG. 2 of the drawings, apparatus and process, the heat required to carry out the same degree of separation of the components of a similar feed stream and at similar rates of feed throughput is 10 to 15% less in the apparatus and process of the present invention.

DESCRIPTION OF THE APPARATUS

The gas-liquid separator tower (4) is a typical gas liquid distillation tower and is sized and operated to carry out the desired gas-liquid separation for the hydrocarbon feed to the separator.

The benzene distillation tower, the xylene distillation tower and external heaters are those that are conventionally used in the art.

The first toluene distillation tower (A) and the second toluene distillation tower (B) and their operating conditions are unique to the present invention. The first toluene distillation tower (A) is operated at a sufficiently high temperature and pressure to provide sufficient heat to the benzene tower heat exchanger for carrying out the distillation in the benzene distillation tower. The integration of the first toluene distillation tower and the benzene tower heat exchanger is also unique to the present invention.

The second toluene distillation tower (B) is operated at a sufficiently low pressure to flash vaporize at least a portion of the toluene feed to the tower (B) and is unique to the present invention.

In a process previously known to applicants, a single toluene distillation tower used to separate a specified amount per hour of feed containing $C_5^-$, benzene, toluene, xylene, ethyl benzene and $C_9^+$ aromatic hydrocarbons is required to be about 80 feet in height and twenty-one feet in diameter to carry out the desired separation of toluene.

In the present invention applicants, by using two toluene distillation towers (A) and (B) for essentially the same amount per hour of hydrocarbon feedstock and degree of separation of the aromatic hydrocarbons, were unexpectedly able to use two about 40-foot high towers having diameters of only about fourteen feet each, and to reduce the overall heat energy requirements in BTU/hr for carrying out the separation process by about 10–15%. It is emphasized that a 10 to 15% savings in heat energy requirement in a distillation separation process of the present type is large, unexpected and unprecedented.

The process and apparatus of the present invention also has the distinct advantage that the two 40-ft. high toluene distillation towers (A) and (B) can be fabricated off-site and brought to the process site for installation, whereas the previously known single 80-foot high toluene distillation tower was required to be fabricated on-site at a considerably higher cost than the two smaller distillation towers.

In accordance with an embodiment of the present invention, an essentially pure toluene stream is fed to a toluene transalkylation reactor to selectively convert the toluene to para-xylene and benzene using a ZSM-5 catalyst in accordance with the processes described in one or more of U.S. Pat. Nos. 4,097,543 to Haag; 4,117,026 to Haag; 4,851,604 to Absil and 5,173,461 to Absil; and 5,243,117 to Chang, which patents are incorporated herein in their entirety by reference thereto.

The toluene transalkylation process is carried out to obtain an about 30% conversion of the toluene feed, to obtain a toluene, benzene and xylene effluent stream which is the feed stream to the separation process of the present invention.

The practice of the process and apparatus of the invention is further described with reference to FIG. 1 of the drawings and the following example.

EXAMPLE

A fresh charge stream of toluene is fed through line 1 together with recycle toluene in lines 18 and 25 to transalkylation reactor 2 and is contacted with a ZSM-5 catalyst under transalkylation reaction conditions to obtain a 30% conversion of the toluene and an aromatic hydrocarbon effluent stream having the following composition based on 1000 parts of effluent.

| Component | Parts |
| --- | --- |
| $C_5^-$ | 12 |
| Benzene | 150 |
| Toluene (unreacted) | 700 |
| Xylene[(1)] | 130 |
| Ethyl benzene | 4 |
| $C_9^+$ aromatics | 4 |

[(1)]The selectivity in the transalkylation reaction to para-xylene is 96.0%. However, the selectivity to para-xylene of the ZSM-5 transalkylation reaction can be in the range of 95% to 99% by weight of the xylene fraction.

The aromatic hydrocarbon stream is fed to the separator tower 4 which is operated at a temperature and a pressure sufficient to distill overhead the $C_5^-$ component of the feed. An overhead fraction containing the $C_5^-$ component in an amount of about 12 parts is removed. A liquid bottom fraction having the following composition is withdrawn.

| Component | Parts |
| --- | --- |
| Benzene | 150 |
| Toluene | 700 |
| Xylene | 130 |
| Ethyl benzene | 4 |
| $C_9^+$ aromatics | 4 |

The bottom fraction from the separator 6 is fed to the benzene distillation tower 7 which is operated at a temperature sufficient to distill overhead all or substantially all of the benzene compound. The heat to carry out the benzene distillation is provided by the benzene heat exchanger 10.

A substantially pure benzene stream in the amount of 150 parts is removed overhead. A bottom fraction is withdrawn and has the following composition.

| Component | Parts |
| --- | --- |
| Toluene | 700 |
| Xylene | 130 |
| Ethyl benzene | 4 |
| $C_9^+$ aromatics | 4 |

The bottom fraction withdrawn from the benzene distillation tower is fed to the first toluene distillation tower (A) which is operated at an elevated temperature and a pressure sufficient to distill overhead a major portion but not all of the toluene component and to provide sufficient heat to the heat exchanger 10 to carry out the benzene distillation in the benzene distillation tower 7.

The heat required to carry out the toluene distillation is provided by the toluene distillation tower external heater 21.

An overhead toluene fraction in the amount of 600 parts is removed and recycled to the transalkylation reactor 2. A liquid bottoms fraction having the following composition is withdrawn.

| Component | Parts |
| --- | --- |
| Toluene | 100 |
| Xylene | 130 |
| Ethyl benzene | 4 |
| $C_9^+$ aromatics | 4 |

The bottom fraction is fed to the second toluene distillation tower (B) which is operated at a temperature and a sufficiently lower pressure such that at least a portion of the toluene is flash vaporized in the second toluene distillation tower.

The heat required to carry out the remainder of the toluene distillation is provided by the second toluene distillation tower heat exchanger 27.

An overhead toluene fraction in the amount of 100 parts is removed and recycled to the transalkylation reactor 2.

A liquid bottom fraction having the following composition is withdrawn.

| Component | Parts |
| --- | --- |
| Xylene | 130 |
| Ethyl benzene | 4 |
| $C_9^+$ aromatics | 4 |

The bottom fraction is fed to the xylene distillation tower which is operated at a temperature sufficient to distill overhead the xylene and ethyl benzene components.

The heat required to carry out the xylene distillation is provided by the xylene distillation tower external heater 38.

An overhead xylene and ethyl benzene fraction in the amount of 130 parts xylene and 4 parts ethyl benzene is removed and taken for further processing to separate the ethyl benzene and to separate the xylene into ortho-, meta- and para-xylene.

A liquid bottom fraction having the following composition is withdrawn.

| Component | Parts |
| --- | --- |
| $C_9^+$ aromatics | 4 |

The $C_9^+$ aromatics contain trimethyl benzene, methyl ethylbenzene, naphthalene etc. and are taken for further treatment or disposal.

The disclosed distillation process is applicable to aromatic hydrocarbon streams containing benzene, toluene and xylene (BTX). The heat energy savings may vary depending on the relative amounts of the benzene, toluene and xylene as well as other components of the stream.

The foregoing description and example illustrate the economic advantages of the process and apparatus integration provided by this invention. In addition to the 10 to 15% savings in heat energy requirement costs per year for a typical size aromatic hydrocarbons (BTX) separation complex, there is a further significant savings present in capital investment for such a plant since the invention eliminates the requirement of fabricating on-site an 80–85 ft. high, 20–21 ft. in diameter toluene distillation tower.

Although this invention has been illustrated by reference to specific embodiments, it will be apparent to those skilled in the art that various changes and modifications may be made which fall within the scope of the claims of this invention.

What is claimed is:

1. An improved distillation process for recovering xylene from an aromatic hydrocarbon stream which comprises:

feeding the hydrocarbon stream to separator tower to remove overhead $C_5^-$ hydrocarbon fraction and withdraw a liquid hydrocarbon bottom fraction containing benzene, toluene, xylene, ethyl benzene and $C_9^+$ aromatic hydrocarbons;

feeding the separator tower liquid hydrocarbon bottom fraction to a benzene distillation tower to remove overhead a benzene fraction and to withdraw a benzene tower liquid bottom fraction containing toluene, xylene, ethyl benzene and $C_9^+$ aromatic hydrocarbons;

feeding the benzene tower liquid bottom fraction to a first toluene distillation tower operated at elevated temperature and elevated pressure to remove overhead a first toluene tower overhead fraction and withdraw a first toluene tower liquid bottom fraction containing remaining toluene, xylene, ethyl benzene and $C_9^+$ aromatic hydrocarbons;

feeding said first toluene overhead fraction to a benzene tower heat exchanger to provide the heat needed to distill the benzene in the benzene distillation tower;

condensing in the benzene lower heat exchanger the first toluene overhead fraction to obtain a first toluene overhead liquid stream;

recycling a portion of the first toluene overhead liquid stream to provide reflux for the first toluene distillation tower, and removing overhead the remaining portion of first toluene overhead liquid stream;

feeding the first toluene tower liquid bottom fraction to a second toluene distillation tower operated at reduced pressure to flash vaporize at least a portion of the toluene, and to remove overhead a second toluene fraction, and withdraw a second liquid bottom fraction containing xylene, ethyl benzene and $C_9^+$ aromatic hydrocarbons;

feeding the second toluene liquid bottom fraction to a xylene distillation tower to remove overhead a stream containing xylene and ethyl benzene and to withdraw a xylene tower liquid bottom fraction containing $C_9^+$ aromatic hydrocarbons;

feeding the xylene distillation tower overhead fraction to a second toluene tower heat exchanger to provide heat for the distillation of the toluene in the second toluene distillation tower;

condensing the xylene tower overhead stream in the second toluene tower heat exchanger and recycling a portion of the condensed overhead stream to provide: reflux for the xylene distillation tower;

removing the remainder of the condensed xylene overhead stream containing xylene and ethyl benzene; and separating the xylene from the ethyl benzene in said condensed xylene overhead stream.

2. The process of claim 1 wherein the aromatic hydrocarbon stream feed to the distillation process is an effluent from a transalkylation reaction process.

3. The process of claim 1 wherein the aromatic hydrocarbon stream feed to the distillation process is an aromatic hydrocarbon petroleum refining stream containing benzene, toluene and xylene.

4. The process of claim 1 wherein the first toluene distillation tower is operated at a sufficiently high temperature and pressure such that the overhead toluene stream contains sufficient heat energy to heat and distill the benzene in the benzene distillation tower, and the second toluene distillation tower is operated at a sufficiently reduced pressure and at a temperature such that at least a portion of the toluene in the second toluene distillation tower is flash vaporized and distilled overhead.

5. The process of claim 1 wherein the heat needed to carry out the distillation in the first toluene distillation tower is supplied by an external heat source.

6. The process of claim 1 wherein the heat needed to carry out the distillation in the xylene distillation tower is supplied by an external heat source.

7. The process of claim 1 wherein the heat extracted by condensing the first toluene overhead stream is used to heat and reboil the bottom fraction in the benzene distillation tower to distill substantially all of the benzene fed to the benzene tower.

8. The process of claim 1 wherein the heat extracted by condensing the xylene tower overhead stream is used to heat and reboil the bottom fraction of the second toluene distillation tower to distill substantially all of the toluene remaining in the feed to the second toluene distillation tower.

9. An apparatus for a distillation process to recover xylene from an aromatic hydrocarbon stream comprising a separator tower to separate $C_5^-$ hydrocarbons fractions overhead and withdraw a bottom fraction containing benzene, toluene, xylene, ethyl benzene and $C_9^+$ aromatic hydrocarbons, connecting means for feeding said liquid bottom fraction to a benzene distillation tower; means for beating and distilling the benzene in the benzene distillation tower and for removing an overhead benzene fraction; means for withdrawing a liquid bottom fraction containing toluene, xylene, ethyl benzene and $C_9^+$ aromatic hydrocarbons; a benzene tower heat exchanger operably connected to the benzene distillation tower to cycle said bottom fraction from said benzene tower to said benzene heat exchanger to provide heat to said bottom fraction to distill said benzene; connecting means for connecting the benzene tower to a first toluene distillation tower to feed the bottom fraction withdrawn from said benzene distillation tower to the first toluene distillation tower operated at elevated temperature and pressure; means for removing a toluene first tower overhead fraction and means for withdrawing a first toluene tower liquid bottom fraction; connecting means for feeding said first toluene overhead fraction to said benzene distillation tower heat exchanger to provide heat to distill the benzene;

connecting means for feeding the first toluene distillation tower liquid bottom fraction containing toluene, xylene, ethyl benzene and $C_9^+$ aromatic hydrocarbons to a second toluene distillation tower and to remove overhead a second toluene distillation tower overhead fraction and to withdraw a second toluene distillation tower liquid bottom fraction;

a second toluene heat exchanger means operably connected to said second toluene distillation tower to provide heat needed to distill toluene from said second toluene distillation tower;

connecting means for feeding the second toluene distillation tower liquid bottom fraction to a xylene distillation tower to remove overhead a xylene fraction and to withdraw a xylene tower bottom fraction;

means for feeding a portion of the xylene overhead fraction to the second toluene distillation tower heat exchanger to condense the overhead fraction and heat the bottom fraction in the second toluene distillation tower heat exchanger and distill the toluene in the second toluene distillation tower;

means for withdrawing the bottom fraction from the xylene distillation tower containing $C_9^+$ aromatic hydrocarbons; and means for removing the xylene overhead fraction; and means for separating the xylene from the ethyl benzene in the recovered xylene overhead fraction.

10. The apparatus of claim 9 wherein means are provided for maintaining an elevated temperature and elevated pressure in the first toluene distillation tower which is sufficient to heat the toluene overhead stream such that the toluene overhead stream contains sufficient heat energy to distill overhead substantially all of the benzene in the feed to the benzene distillation tower.

11. The apparatus of claim 9 wherein means are provided for maintaining a temperature and a lower pressure, in the second toluene distillation tower, relative to the pressure in the first toluene distillation tower, such that at least a portion of the toluene feed to the second toluene distillation tower is flash vaporized and distilled overhead.

12. The apparatus of claim 9 wherein the heat needed to carry out the distillation in the first toluene distillation tower is provided by an external heat source.

13. The apparatus of claim 9 wherein the heat needed to carry out the distillation in the xylene distillation tower is provided by an external heat source.

14. The apparatus of claim 9 wherein the heat required to carry out the benzene tower distillation is provided by the benzene heat exchanger which is operably connected to receive the overhead fraction from the first toluene distillation tower and to receive heat from the said overhead fraction.

15. The apparatus of claim 9 wherein the heat required to carry out the second toluene tower distillation is provided by the second toluene tower heat exchanger which is operably connected to receive the overhead fraction from the xylene distillation tower and to receive heat from the said overhead fraction, wherein said overhead fraction contains sufficient heat energy to carryout the distillation of the remaining toluene in the feed to the second toluene distillation tower.

* * * * *